US00PP21626P2

(12) United States Plant Patent
Sanders

(10) Patent No.: US PP21,626 P2
(45) Date of Patent: Jan. 11, 2011

(54) *AGERATUM* PLANT NAMED 'AGROS'

(50) Latin Name: *Ageratum houstonanium*
Varietal Denomination: Agros

(75) Inventor: Monica Maria Adelheid Sanders, Grootebroek (NL)

(73) Assignee: Syngenta Crop Protection AG, Basel (CH)

( * ) Notice: Subject to any disclaimer, the term of this patent is extended or adjusted under 35 U.S.C. 154(b) by 0 days.

(21) Appl. No.: 12/459,893

(22) Filed: Jul. 9, 2009

(51) Int. Cl.
*A01H 5/00* (2006.01)

(52) U.S. Cl. ..... Plt./400

(58) Field of Classification Search ..... Plt./400
See application file for complete search history.

(56) References Cited

PUBLICATIONS

Upov-rom GTITM, Plant Variety Database 2010/02, GTI Jouve Retrieval Software, Citation for *Ageratum* 'Agros' one page.*

* cited by examiner

*Primary Examiner*—June Hwu
(74) *Attorney, Agent, or Firm*—S. Matthew Edwards

(57) ABSTRACT

A new *Ageratum* plant named 'Agros,' particularly distinguished by the purple flowers, early and continuously flowering and has a habit that is compact, upright while mounded and is freely branching.

1 Drawing Sheet

Latin name of the genus and species of the plant claimed: *Ageratum houstonanium.*

Varietal denomination: 'Agros'.

BACKGROUND OF THE NEW PLANT

The present invention comprises a new *Ageratum*, botanically known as *Ageratum houstonanium*, and hereinafter referred to by the variety name 'Agros'.

'Agros' is a product of a planned breeding program. The new cultivar 'Agros' has purple flowers, early and continuously flowering and has a habit that is compact, upright while mounded and is freely branching.

'Agros' originated from a hybridization in a controlled breeding program in Enkhuizen, Netherlands. The female parent was an unpatented seedling identified as 'X52-2' with light purple color. 'X52-2' has a more vigorous habit than 'Agros'.

The male parent of 'Agros' was an unpatented hybrid seedling identified as '54-1' with purple color. '54-1' has a more vigorous habit than 'Agros'.

'Agros' was selected as one flowering plant within the progeny of the stated cross in August 2003. The pollination took place in September 2002 and the seed sowing in March 2003, all in a controlled environment in Enkhuizen, Netherlands.

The first act of asexual reproduction of 'Agros' was accomplished when vegetative cuttings were taken from the initial selection in August 2003 in a controlled environment in Enkhuizen, Netherlands.

Horticultural examination of plants grown from cuttings of the plant initiated in early spring 2004 in Enkhuizen, Netherlands; Gilroy, Calif. USA; and Angers, France, and continuing thereafter, has demonstrated that the combination of characteristics as herein disclosed for 'Agros' are firmly fixed and are retained through successive generations of asexual reproduction.

'Agros' has not been observed under all possible environmental conditions. The phenotype may vary significantly with variations in environment such as temperature, light intensity and day length.

A Plant Breeder's Right for this cultivar was granted in the European Union on Oct. 22, 2007. 'Agros' has not been made publicly available more than one year prior to the filing of this application.

BRIEF DESCRIPTION OF THE PHOTOGRAPH

The accompanying photographic drawing shows typical flower and foliage characteristics of 'Agros' with colors being as true as possible with an illustration of this type. The photographic drawing shows a flowering potted plant of the new variety. This photograph was taken in May 2005 in Enkhuizen, Netherlands.

DETAILED BOTANICAL DESCRIPTION

The measurements were taken in Enkhuizen, Netherlands, in the summer of 2008 on plants that were growing in field trials. These plants were 30 weeks old. The color readings were taken in a laboratory under ambient light.

Color Chart used: Royal Horticultural Society Colour Chart (R.H.S.) 2001.

BRIEF SUMMARY OF INVENTION

The following observations, measurements, and comparisons describe plants grown under natural light and artificial light in a greenhouse in Enkhuizen, Netherlands. The following traits have been repeatedly observed and are determined to be basic characteristics of the new variety. The combination of these characteristics distinguishes this *Ageratum* as a new and distinct variety.

TABLE 1

DIFFERENCES BETWEEN THE NEW VARIETY 'AGROS' AND A SIMILAR VARIETY

| | 'Agros' | 'Agrosamtis' (U.S. Plant Pat. No. 15,631) |
|---|---|---|
| Flower size | Medium | Small |
| Leaf size | Small to medium | Small |
| Flower color | Mid purple | Light purple with near white pistils |

Plant:

*Form, growth and habit.*—Compact and mounding, freely branching and lateral branching at every node.

*Plant height.*—19 cm.

*Plant width.*—39 cm.

Roots:

*Type of roots.*—Fibrous. Roots start to grow on every part of the stem that contacts de soil, so not only at the nodes.

Foliage:

*Type.*—Opposite, decusate.

*Immature, leaf color, upper surface.*—RHS N134A.

*Lower surface.*—RHS 141B.

*Mature, leaf color, upper surface.*—RHS N134A.

*Lower surface.*—RHS 141B.

*Length.*—4.2 cm.

*Width.*—3.9 cm.

*Shape.*—Ovate.

*Base shape.*—Cordate.

*Apex shape.*—Acute.

*Margin.*—Serrate.

*Texture.*—Both sides slightly pubescent.

*Color of veins, upper surface.*—RHS 144A.

*Color of veins, lower surface.*—RHS 144A.

*Petioles color.*—RHS 144A.

*Petioles length.*—0.4 cm.

*Diameter of petiole.*—0.2 cm.

*Texture.*—Slightly pubescent.

Stem:

*Color of stem.*—RHS 145A.

*Length of stem.*—22.0 cm.

*Diameter.*—0.4 cm.

*Length of internodes.*—3.3 cm.

*Texture.*—Slightly pubescent.

*Color of peduncle.*—RHS 146A.

*Length of peduncle.*—0.7 cm.

*Peduncle diameter.*—0.2 cm.

*Texture.*—Slightly pubescent.

*Color of pedicel.*—RHS 146A.

*Length of pedicel.*—0.5 cm.

*Pedicel diameter.*—0.1 cm.

*Texture.*—Slightly pubescent.

Inflorescence:

*Type.*—Compound umbel of capitula.

*Capitulum in bud stage.*—Round, flat capitulum, showing unopened florets from the start.

*Quantity of inflorescences.*—130-140.

*Average diameter of the umbel.*—About 4.0 cm.

*Lastingness of individual blooms on the plant.*—The capitula of one umbel open over a period of 3-4 weeks.

*Fragrance.*—None.

*Number of capitula per inflorescence.*—9-12.

*Number of disc florets per capitulum.*—90.

*Number of ray florets.*—0.

*Shape of the corolla of the disk floret.*—Actinomorph.

*Apex shape.*—5 pointed, star shape.

*Length of disc floret.*—Less than 0.1 cm.

*Diameter of disc floret.*—Less than 0.1 cm.

*Color of disc floret upper side.*—RHS 72B.

*Color of disc floret lower side.*—RHS 155C.

*Diameter of capitulum at beginning of flowering.*—0.5 cm.

*Depth of capitulum.*—0.7 cm.

*Color of capitulum at beginning of flowering.*—RHS N78A.

*Color of capitulum at full flowering.*—RHS N77B.

*Diameter of capitulum at full flowering.*—0.6 cm.

*Receptacle height.*—0.5 cm.

*Receptacle diameter.*—0.9 cm.

*Number of phyllaries per capitulum.*—21.

*Color of phyllaries — upper side.*—RHS 132A with tip RHS 185A.

*Color of phyllaries — inner side.*—RHS 132C with tip RHS 185B.

*Length of phyllaries.*—0.3 cm.

*Diameter of phyllaries.*—Less than 0.1 cm.

*Shape of phyllaries.*—Lanceolate.

*Texture of phyllaries.*—Scabrous.

Reproductive organs:

*Number of pistils.*—1.

*Shape of pistils.*—Style with two filiform branches.

*Length of stigma and style.*—0.7 cm.

*Color of stigma.*—RHS 72A.

*Inferior ovary.*—5 ribbed.

*Pappus.*—Short.

*Number of anthers.*—5, connate in a tube, filaments free.

*Shape of anthers.*—Ecalcarate.

*Pollen amount.*—A little pollen is present.

*Color of pollen.*—RHS 155D.

*Seed set.*—Some seed set.

Seed:

*Shape.*—Pentagonal.

*Length.*—0.2 cm.

*Diameter.*—Less than 0.1 cm.

*Color.*—RHS 202A.

*Pappus.*—Very short.

*Physiological and ecological characteristics.*—Good tolerance to heat and cold, but no frost tolerance.

*Disease/pest resistance.*—Has not been observed.

What is claimed is:

1. A new and distinct variety of *Ageratum* plant named 'Agros,' substantially as illustrated and described herein.

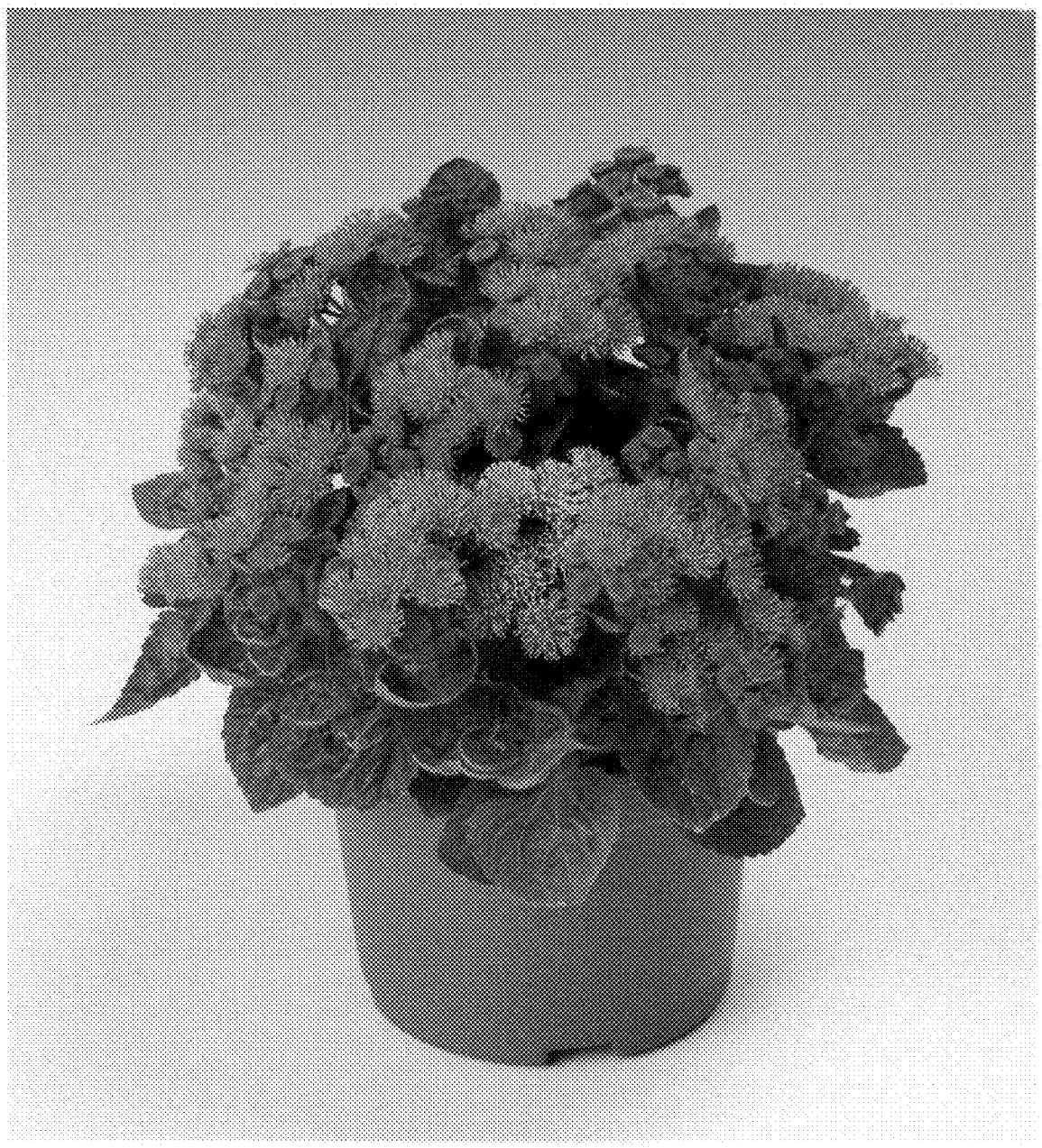

* * * * *